United States Patent [19]

Kraatz et al.

[11] Patent Number: 4,783,538

[45] Date of Patent: Nov. 8, 1988

[54] PROCESS FOR THE PREPARATION OF OPTICALLY ACTIVE AZOLYL-CARBINOL DERIVATIVES, OPTICALLY ACTIVE 2-(4CHLORO-PHENOXYMETHYL)-3,3-DIMETHYL-1-(1,2,4-TRIAZOL-1-YL)-2-BUTANOL, PREPARED BY THIS PROCESS AND ITS USE AS AN ANTIMYCOTIC

[75] Inventors: Udo Kraatz, Leverkusen; Graham Holmwood; Dieter Berg, both of Wuppertal; Manfred Plempel, Haan, all of Fed. Rep. of Germany

[73] Assignee: Bayer Aktiengesellschaft, Leverkusen, Fed. Rep. of Germany

[21] Appl. No.: 791,237

[22] Filed: Oct. 25, 1985

[30] Foreign Application Priority Data

Nov. 2, 1984 [DE] Fed. Rep. of Germany ....... 3440118
Nov. 2, 1984 [DE] Fed. Rep. of Germany ....... 3440112

[51] Int. Cl.$^4$ .................. C07D 249/08; C07D 233/60
[52] U.S. Cl. ..................................... 548/262; 548/336; 548/341
[58] Field of Search ............... 548/262, 336, 341; 549/559

[56] References Cited

U.S. PATENT DOCUMENTS 4,036,970 7/1977 Walker et al. .............. 548/341
4,560,697 12/1985 Richardson et al. ........... 548/262
4,622,335 11/1986 Kramer et al. ............... 548/262

FOREIGN PATENT DOCUMENTS 0047594 8/1981 European Pat. Off. ........... 548/262
0040345 11/1981 European Pat. Off. ........... 548/262
0043419 1/1982 European Pat. Off. ........... 548/262
0054431 6/1982 European Pat. Off. ........... 548/262
0089922 9/1983 European Pat. Off. ........... 548/262
0098942 1/1984 European Pat. Off. ........... 548/262
2080795 2/1982 United Kingdom ............... 548/262

OTHER PUBLICATIONS

Nohira, "Optically Active Carboxylic Acids and Esters", CA 99:194439n (1983).

*Primary Examiner*—Robert T. Bond
*Assistant Examiner*—P. L. Morris
*Attorney, Agent, or Firm*—Sprung Horn Kramer & Woods

[57] ABSTRACT

A process for the preparation of optically active azolyl-carbinol derivatives having antimycotic fungicidal and plant growth regulating properties from racemic mixtures thereof. The (−)-enantiomer of 2-(4-chloro-phenoxymethyl)-3,3-dimethyl-1-(1,2,4-triazol-1-yl)-2-butanol of the formula

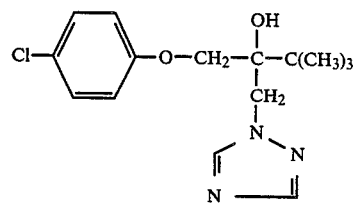

is prepared.

8 Claims, No Drawings

PROCESS FOR THE PREPARATION OF OPTICALLY ACTIVE AZOLYL-CARBINOL DERIVATIVES, OPTICALLY ACTIVE 2-(4CHLORO-PHENOXYMETHYL)-3,3-DIMETHYL-1-(1,2,4-TRIAZOL-1-YL)-2-BUTANOL, PREPARED BY THIS PROCESS AND ITS USE AS AN ANTIMYCOTIC

The present invention relates to a new process for the preparation of optically active azolylcarbinol derivatives of racemic azolylcarbinol derivatives, most of which are known. The optically active derivatives have antimycotic, fungicidal and plant growth-regulating properties.

It has already been disclosed that certain racemic azole derivatives can be resolved into optical antipodes by the classical route of reacting them in a first stage with optically active acids, optionally in the presence of a diluent; the corresponding salts are then separated in a second stage on the basis of their different solubilities, and thereafter the optical antipodes are liberated in a third stage from the corresponding salts with the aid of bases, if appropriate in the presence of a diluent (see, for example, EP-OS (European Published Specification) No. 0,004,918 and DE-OS (German Published Specification) No. 3,302,122). However, this process cannot be applied to all azole derivatives. As our own experiments have shown, it is not possible to prepare crystalline salts of β-hydroxyethylazolyl derivatives of the type of the compounds of the formula (I) with optically active acids.

It is also known that epoxides can be opened with acids (see Houben-Weyl, Methoden der organischen Chemie (Methods of organic chemistry), volume VI/3, page 448 et seq. (1965)). However, this process also cannot be applied to all epoxides. As our own experiments have shown, it is not possible to open epoxides of the type of the compounds of the formula (II) with optically active acids such as, for example, mandelic acid or tartaric acid. It was possible to achieve the desired reaction only by adding boron trifluoride-etherate to the reaction solution.

It is furthermore known that optically active 3-alkylthio-2-dichlorophenyl-1-imidazol-1-yl-2-propanol of the formula

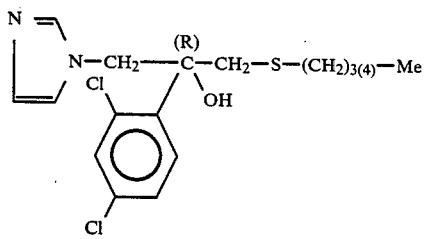

can be obtained by hydrolyzing the corresponding epoxides in a first stage; the corresponding diols are esterified in a second stage with optically active acids, such as, for example, lactic acid; in a third stage, the diastereomeric esters are separated and hydrolyzed; the corresponding sulphonate is prepared in a fourth stage; and in a fifth stage the sulphonate is reacted with alkylmercaptan. This process has the disadvantage that it is a multistage reaction.

It has now been found that the optically active azolylcarbinol derivatives of the formula

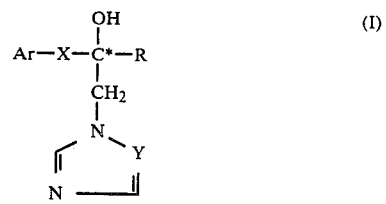

in which
Ar represents optionally substituted phenyl,
R represents optionally substituted alkyl, optionally substituted cycloalkyl or optionally substituted phenyl,
X represents the groupings —OCH$_2$—, —SCH$_2$—, —CH$_2$CH$_2$—, —CH=CH— or —C≡C— or a direct bond and
Y represents a nitrogen atom or the CH group, are obtained by a process in which, in a *first stage* racemic oxiranes of the formula (II)

in which
Ar, R and X have the abovementioned meaning, are reacted with optically active sulphonic acids, if appropriate in the presence of a diluent, and the diastereomeric ester mixture formed is separated into the pure diastereomeric components; and, in a *2nd stage*, reaction is carried out with 1,2,4-triazole or imidazole in the presence of a base.

It is extremely surprising that the optically active azolylcarbinol derivatives of the formula (I) can be prepared in a high yield by the process according to the invention. On the basis of the prior art, it was to be expected that the desired ring opening does not occur without a catalyst, such as, for example, boron trifluoride-etherate.

The process according to the invention has the advantage that optical antipodes can also be obtained in high yields from those azolyl derivatives with which the classical method of racemic resolution was not successful.

The optically active azolylcarbinol derivatives of the formula (I) have good biological activity, individual antipodes having better activity than the corresponding racemates. Thus, for example, the (−)-enantiomer of 2-(4-chlorophenoxymethyl)-3,3-dimethyl-1-(1,2,4-triazol-1-yl)-1-butanol displays a more powerful inhibition of sterol synthesis than the corresponding racemate, coupled with a very good general antimycotic activity.

Formula (I) provides a general definition of the optically active azolylcarbinol derivatives which can be prepared by the process according to the invention. In this formula, preferably,
Ar represents phenyl which is optionally mono-, di- or tri-substituted by identical or different substituents, preferred substituents which may be mentioned being: halogen, alkyl with 1 to 4 carbon atoms, alkoxy and alkylthio with in each case 1 or 2 carbon atoms, nitro, and halogenoalkyl, halogenoalkoxy and halogenoalkylthio with in each case 1 or 2 carbon atoms and 1 to 5 identical or different halogen atoms, such as, preferably, fluorine and chlorine atoms, or phenyl phenoxy, benzyl or benzyloxy, each of which is optionally substituted by halogen and/or alkyl with 1 or 2 carbon atoms, or the —CH=NOZ radical, wherein Z represents hydrogen, straight-chain or branched alkyl with 1 to 6 carbon atoms, alkenyl or alkynyl with in each case 2 to 6 carbon atoms, or benzyl which is optionally mono-, di- or tri-substituted by identical or different substituents from the group comprising halogen and alkyl with 1 or 2 carbon atoms;

R represents the groupings

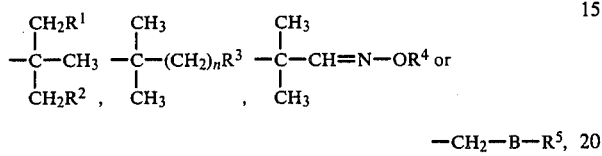

$$-CH_2-B-R^5,$$

or represents cycloalkyl which has 3 to 7 carbon atoms and is optionally substituted by alkyl with 1 or 2 carbon atoms, or represents cyclopropyl which is substituted by triazolyl or imidazolyl, or represents phenyl which is optionally mono-, di- or tri-substituted by identical or different substituents, possible substituents on the phenyl being the substituents on phenyl which have already been mentioned for Ar; wherein $R^1$ represents hydrogen, fluorine, chlorine or bromine;

$R^2$ represents fluorine, chlorine or bromine;

$R^3$ represents alkyl, alkoxy or alkylthio with in each case 1 to 4 carbon atoms, halogenoalkoxy or halogenoalkylthio with in each case 1 or 2 carbon atoms and 1 to 5 identical or different halogen atoms, such as fluorine and chlorine atoms, alkenyl with 2 to 6 carbon atoms, alkoxycarbonyl with 1 to 4 carbon atoms in the alkyl part, or cyano, or represents phenyl, phenoxy, phenylthio, benzyloxy or benzylthio, each of which is optionally mono-, di- or tri-substituted by identical or different substituents, preferred substituents on the phenyl which may be mentioned in each case being: halogen, alkyl with 1 to 4 carbon atoms, alkoxy and alkylthio with in each case 1 or 2 carbon atoms, halogenoalkyl, halogenoalkoxy and halogenoalkylthio with in each case 1 or 2 carbon atoms and 1 to 5 identical or different halogen atoms, such as, preferably, fluorine and chlorine atoms, dialkylamino with 1 to 4 carbon atoms in each alkyl part, nitro, cyano, alkoxycarbonyl with 1 to 4 carbon atoms in the alkyl part, and phenyl which is optionally substituted by halogen;

n represents the numbers 0, 1 or 2;

$R^4$ represents straight-chain or branched alkyl with 1 to 6 carbon atoms or alkenyl or alkynyl with in each case 2 to 6 carbon atoms, or represents phenylalkyl which has 1 or 2 carbon atoms in the alkyl part and is optionally mono-, di- or tri-substituted by identical or different substituents, possible substituents on the phenyl being the substituents on phenyl which have already been mentioned for Ar;

$R^5$ represents straight-chain or branched alkyl with 1 to 4 carbon atoms; and

B represents oxygen or sulphur;

X represents the groupings —OCH$_2$—, —SCH$_2$—, —CH$_2$CH$_2$—, —CH=CH— and —C≡C— or a direct bond; and Y represents a nitrogen atom or the CH group.

Particularly preferred compounds of the formula (I) are those in which

Ar represents phenyl which is optionally mono- or di-substituted by identical or different substituents, substituents which may be mentioned being: fluorine, chlorine, bromine, methyl, ethyl, isopropyl, tert.-butyl, methoxy, methylthio, trifluoromethyl, trifluoromethoxy, trifluoromethylthio, methoximinomethyl, butoximinomethyl and 1-methoxyiminoethyl, and phenyl, phenoxy, benzyl or benzyloxy, each of which is optionally substituted by fluorine, chlorine and/or methyl;

R represents the groupings

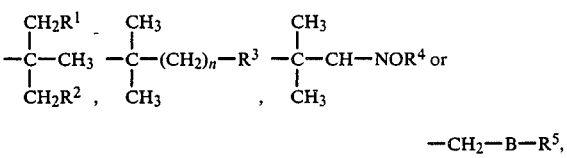

$$-CH_2-B-R^5,$$

or represents cyclopropyl, cyclopentyl or cyclohexyl, each of which is optionally substituted by methyl or ethyl, or represents 1-(1,2,4-triazol-1-yl)- or (imidazol-1-yl)-1-cyclopropyl, or represents phenyl which is optionally mono- or di-substituted by identical or different substituents from the group comprising fluorine, chlorine, methyl and trifluoromethyl, $R^1$ represents hydrogen, fluorine or chlorine;

$R^2$ represents fluorine or chlorine;

$R^3$ represents methyl, ethyl, propyl, methoxy, ethoxy, methylthio, ethylthio, trifluoromethoxy, trifluoromethylthio, vinyl, methoxycarbonyl, ethoxycarbonyl or cyano, or represents phenyl, phenoxy, phenylthio, phenylmethoxy or phenylmethylthio, each of which is optionally mono- or di-substituted by identical or different substituents, substituents on the phenyl which may be mentioned in each case being: fluorine, chlorine, methyl, ethyl, methoxy, methylthio, trifluoromethyl, trifluoromethoxy, trifluoromethylthio, dimethylamino methoxycarbonyl or ethoxycarbonyl, n represents the numbers 0, 1 or 2;

$R^4$ represents methyl, ethyl, n-propyl, n-butyl, allyl or propargyl, or represents benzyl which is optionally mono- or di-substituted by identical or different substituents from the group comprising fluorine, chlorine, methyl, trifluoromethyl and trifluoromethoxy;

$R^5$ represents methyl, ethyl, isopropyl, n-propyl, n-butyl or isobutyl;

B represents oxygen or sulphur;

X represents the groupings —OCH$_2$—, —SCH$_2$—, —CH$_2$CH$_2$—, —CH=CH— or —C≡C— or a direct bond and Y represents a nitrogen atom or the CH group.

Especially preferred compounds of the formula (I) are those in which

Ar represents phenyl which is mono- or di-substituted by identical or different radicals from the group comprising fluorine, chlorine and phenyl, R represents the radical

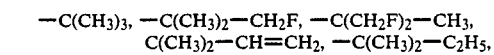

-continued

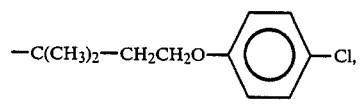

$-C(CH_3)_2-CH=NOCH_3$, $-C(CH_3)_2-CH=NOC_4H_9$,

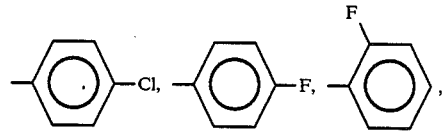

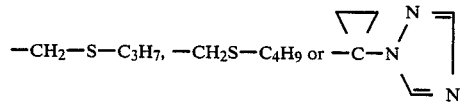

and
X and Y have the meaning given in the definition of the invention.

The following azolylcarbinol derivatives of the formula (I)

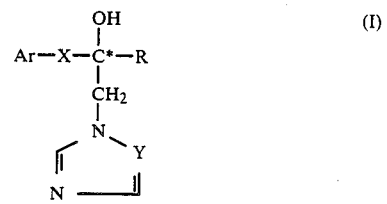

may be mentioned as examples:

| Ar | X | R | Y |
|---|---|---|---|
| Cl-⬡- | $-CH_2CH_2-$ | $-C(CH_3)_3$ | N |
| ⬡-⬡- | $-OCH_2-$ | $-C(CH_3)_3$ | N |
| Cl-⬡- | $-CH=CH-$ | $-C(CH_3)_3$ | N |
| Cl-⬡- | $-OCH_2-$ | $-C(CH_3)_2CH_2F$ | N |
| Cl-⬡- | $-OCH_2-$ | $-C(CH_2F)_2CH_3$ | N |
| Cl-⬡- | $-C\equiv C-$ | $-C(CH_3)_3$ | N |
| Cl-⬡- | $-C\equiv C-$ | $-C(CH_3)_2CH_2F$ | N |
| Cl-⬡- | $-C\equiv C-$ | $-C(CH_2F)_2CH_3$ | N |
| Cl-⬡- | $-OCH_2-$ | $-C(CH_3)_2CH=CH_2$ | N |

-continued

| Ar | X | R | Y |
|---|---|---|---|
| 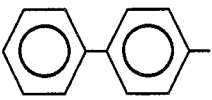 | —OCH$_2$— | —C(CH$_3$)$_2$CH=CH$_2$ | N |
|  | —OCH$_2$— | —C(CH$_3$)$_2$CH$_2$CH$_2$—O—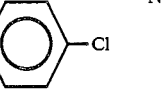—Cl | N |
|  | —OCH$_2$— | —C(CH$_3$)$_2$C$_2$H$_5$ | N |
| 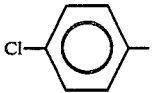 | — | —C(CH$_3$)$_2$—CH=NOCH$_3$ | N |
|  | — | —C(CH$_3$)$_2$—CH=NOC$_4$H$_9$ | N |
| 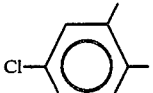 | — | —CH$_2$—S—C$_3$H$_7$ | CH |
| 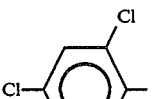 | — | —CH$_2$—S—C$_4$H$_9$ | CH |
|  | — | 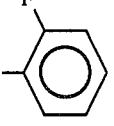 | N |
|  | — | 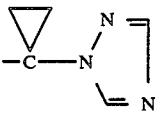 | N |

Formula (II) provides a general definition of the oxiranes requires as starting substances in the process according to the invention. In this formula, Ar, R and X preferably have the meanings which have already been mentioned as preferred for these radicals in connection with the description of the compounds of the formula (I).

Most of the oxiranes of the formula (II) are known (see, for example, EP-OS (European Published Specification) No. 0,040,345, EP-OS (European Published Specification) No. 0,015,756, EP-OS (European Published Specification) No. 0,052,424, EP-OS (European Published Specification) No. 0,054,974, EP-OS (European Published Specification) No. 0,061,835, EP-OS (European Published Specification) No. 0,084,834, EP-OS (European Published Specification) No. 0,110,048 and EP-PS (European Published Specification) No. 0,108,995; some of them are the subject of an Application which has been filed by the assignee of this application and has not yet been published (see German Patent Application No. P 33 34 779 of 26th Sept. 1983); and some of them are the subject of a parallel German Patent Application, No. P34 40 112.1, filed Nov. 2, 1984. They can be obtained in the customary manner by epoxidization of the corresponding ketones (in this context, see the abovementioned patent applications).

Most of the racemic compounds corresponding to the optically active azolylcarbinol derivatives of the formula (I) are likewise known (see the abovementioned European patent applications); some of them are also the subject of an application which has been filed by the assignee of this application and has not yet been published (see the abovementioned German patent application); or they are also the subject of a parallel patent application, No. P34 40 112.1, filed Nov. 2, 1984.

In carrying out the process according to the invention, the oxiranes of the formula (II) are reacted with optically active sulphonic acids in the 1st stage. These acids include, preferably, champhor-10-sulphonic acid, 3-bromo-10-camphorsulphonic acid and 3-bromo-8-camphorsulphonic acid.

In certain cases, other strong optically active acids can also be employed. Acids which may be mentioned in particular here are optically active phosphoric acids, such as, for example, 1,1'-binaphthyl-2,2'-diyl phosphate of the formula

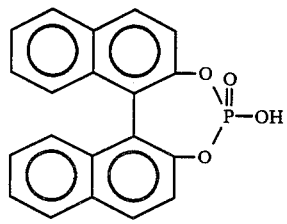

Possible diluents in carrying out the first stage of the process according to the invention are inert organic solvents. These include, preferably, nitriles, such as acetonitrile; ketones, such as methyl ethyl ketone or acetone; ethers, such as tetrahydrofuran or dioxane; and halogenated hydrocarbons, such as chloroform or methylene chloride.

The reaction temperatures can be varied within a substantial range in carrying out the first stage of the process according to the invention. The reaction is in general carried out at temperatures between 0° and 100° C., preferably between 10° and 60° C.

Equimolar amounts are preferably used for carrying out the first stage of the process according to the invention. The two diastereomeric compounds are separated in the customary manner on the basis of different physicochemical properties, such as, for example, by fractional crystallisation or chromatographic separation methods.

Possible diluents in carrying out the second stage of the process according to the invention are likewise inert organic solvents. These include, preferably, nitriles, such as acetonitrile; alcohols, such as ethanol or propanol;.ketones, such as methyl ethyl ketone or acetone; esters, such as ethyl acetate; ethers, such as tetrahydrofuran or dioxane; and amides, such as dimethylformamide.

Possible bases in carrying out the second stage of the process according to the invention are all the inorganic and organic bases which are usually employed. These include, preferably, alkali metal carbonates, such as, for example, sodium carbonate and potassium carbonate; alkali metal hydroxides, such as, for example, sodium hydroxide; alkali metal alcoholates, such as, for example, sodium methylate and ethylate and potassium methylate and ethylate; alkali metal hydrides, such as, for example, sodium hydride; and lower tertiary alkylamines, cycloalkylamines and aralkylamines, such as, in particular, triethylamine.

The reaction temperatures can be varied within a substantial range in carrying out the second stage of the process according to the invention. In general, the reaction is carried out at temperatures between 0° and 150° C., preferably between 40° and 120° C.

In carrying out the second stage of the process according to the invention, 1 to 4 moles of azole and, if appropriate, 1 to 2 moles of base are preferably employed per mole of ester. The end product is isolated in the generally customary manner.

The optically active azolylcarbinol derivatives which can be prepared by the process according to the invention exhibit outstanding biological action, individual antipodes having a better activity than the corresponding racemate.

The present invention furthermore relates to the new (—)-enantiomer of 2-(4-chlorophenoxymethyl)-3,3-dimethyl-1-(1,2,4-triazol-1-yl)-2-butanol, a process for its preparation and its use as an antimycotic.

It has already been disclosed that racemic 2-(4-chlorophenoxymethyl)-3,3-dimethyl-1-(1,2,4-triazol-1-yl)-2-butanol has good antimycotic properties (compare EP-OS European Published Specification) No. 0,043,419). However, the pharmacological properties of this compound differ for the enantiomers isolated.

The (—)-enantiomer of 2-(4-chlorophenoxymethyl)-3,3-dimethyl-1-(1,2,4-triazol-1-yl)-2-butanol of the formula

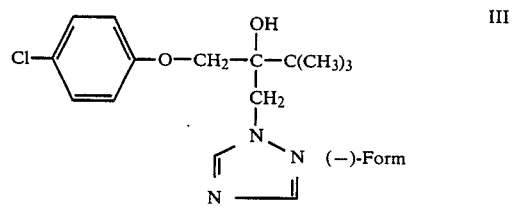

as a new compound, and physiologically acceptable acid addition salts thereof have now been found.

It has furthermore been found that the (—)-enantiomer of 2-(4-chlorophenoxymethyl)-3,3-dimethyl-1-(1,2,4-triazol-1-yl)-butanol is obtained in a good yield and high purity by a process in which, in a 1st stage, a racemic 2-(4-chlorophenoxymethyl)-2-tert.-butyl-oxirane of the formula

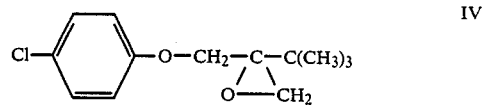

is reacted with strong optically active acids, if appropriate, in the presence of a diluent, and the diastereomeric ester mixture formed is separated into the pure diastereomeric components; and, in a 2nd stage, reaction is carried out with 1,2,4-triazole in the presence of a diluent and, if appropriate, in the presence of a base.

Surprisingly, the (—)-enantiomer of 2-(4-chlorophenoxymethyl)-3,3-dimethyl-1-(1,2,4-triazol-1-yl)-2-butanol of the formula (III) displays, in particular, a more powerful inhibition of sterol synthesis and thus better pharmacological properties than the known corresponding racemate, coupled with a very good general antimycotic activity. The substance according to the invention thus represents a valuable pharmaceutical material.

If, in addition to 2-(4-chlorophenoxymethyl)-2-tert.-butyl-oxirane as the starting substance, d(+)-camphor-10-sulphonic acid is used as the optically active acid, the course of the reaction can be represented by the following equation:

1st stage

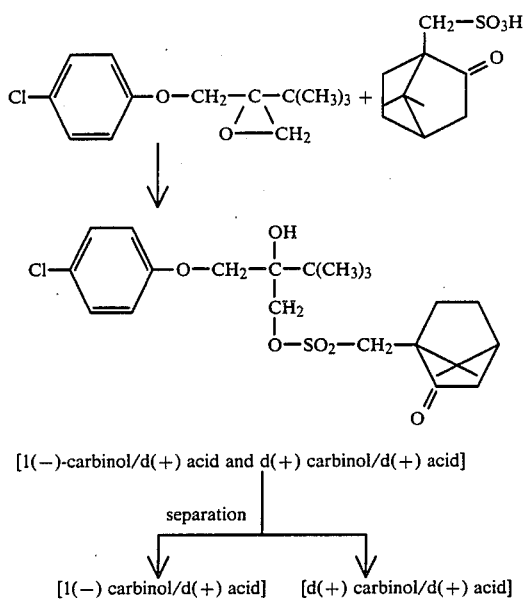

[1(−)-carbinol/d(+) acid and d(+) carbinol/d(+) acid]

separation

[1(−) carbinol/d(+) acid]    [d(+) carbinol/d(+) acid]

2nd stage

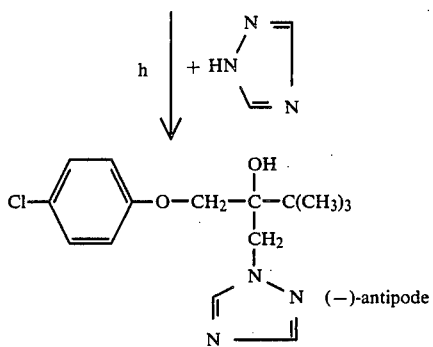

The racemic 2-(4-chlorophenoxymethyl)-2-tert.-butyl-oxirane of the formula to be used as the starting substance is known (compare, for example, EP-OS (European Published Specification) No. 0,040,345).

The acid addition salts of the compound of the formula (III) can be obtained in a simple manner by customary salt bonding methods, for example by dissolving the compound of the formula (III) in a suitable inert solvent and adding the acid, for example hydrochloric acid, and they can be isolated in a known manner, for example by filtration, and, if appropriate, purified by washing with an inert organic solvent.

Preferred acids which can be added on include hydrogen halide acids, such as, for example, hydrochloric acid, and furthermore phosphonic acid, nitric acid, monofunctional and bifunctional carboxylic acids and hydroxycarboxylic acids, such as, for example, acetic acid, maleic acid, succinic acid, fumeric acid, tartaric acid, citric acid, salicylic acid, sorbic acid and lactic acid, and sulphonic acid, such as p-toluenesulphonic acid and 1,4-naphthalenedisulphonic acid.

The compound of the formula (III) according to the invention and its acid addition salts have antimicrobial actions, in particular powerful antimycotic actions. They possess a very broad antimycotic action spectrum, especially against dermatophytes and blastomyces as well as biphase fungi, for example against Candida species, such as *Candida albicans*, Epidermophyton species, such as *Epidermophyton floccosum*, Aspergillus species, such as *Aspergillus niger* and *Aspergillus fumigatus*, Trichophyton species, such as *Trichophyton mentagrophytes*, microsporon species, such as *Microsporon felineum*, and Torulopsis species, such as *Torulopsis glabrata*. The listing of these microorganisms in no way implies a limitation of the germs which can be combated, but is only illustrative.

Examples which may be mentioned of indications in human medicine are, for example: dermatomycoses and systemic mycoses caused by *Trichophyton mentagrophytes* and other trichophyton species, Microsporonspecies, *Epidermophyton floccosum*, blastomyces and biphase fungi as well as moulds.

Examples which may be mentioned as field of indication in veterinary medicine are: all dermatomycoses and systemic mycoses, in particular those which are caused by the abovementioned pathogens.

The present invention includes pharmaceutical formulations which, in addition to non-toxic, inert pharmaceutically suitable excipients, contain one or more active compounds according to the invention or consist of one or more active compounds according to the invention.

The present invention also includes pharmaceutical formulations in dosage units. This means that the formulations are in the form of individual parts, for example tablets, dragees, capsules, pills, suppositories and ampoules, of which the content of active compound corresponds to a fraction or a multiple of an individual dose. The dosage units can contain, for example, 1, 2, 3 or 4 individual doses or a ½, ⅓ or ¼ of an individual dose. An individual dose preferably contains the amount of active compound which is given in one administration and which usually corresponds to a whole, one half, one third or one quarter of a daily dose.

By non-toxic, inert pharmaceutically suitable excipients there are to be understood solid, semi-solid or liquid diluents, fillers and formulation auxiliaries of every kind.

Tablets, dragees, capsules, pills, granules, suppositories, solutions, suspensions and emulsions, pastes, ointments, gels, creams, lotions, powders and sprays may be mentioned as preferred pharmaceutical formulations.

Tablets, dragees, capsules, pills and granules can contain the active compound or compounds in addition to the customary excipients, such as (a) fillers and extenders, for example starches, lactose, sucrose, glucose, mannitol and silica, (b) binders, for example carboxymethylcellulose, alginates, gelatin and polyvinylpyrrolidone, (c) humectants, for example glycerol, (d) disintegrating agents, for example agar-agar, calcium carbonate and sodium bicarbonate, (e) solution retarders, for example paraffin, and (f) absorption accelerators, for example quaternary ammonium compounds, (g) wetting agents, for example cetyl alcohol and glycerol monostearate, (h) absorbents, for example kaolin and bentonite, and (i) lubricants, for example talc, calcium stearate, magnesium stearate and solid polyethylene glycols, or mixtures of the substances listed under (a) to (i).

The tablets, dragees, capsules, pills and granules can be provided with the customary coatings and shells, optionally containing opacifying agents, and can also be of such composition that they release the active compound or compounds only, or preferentially, in a certain part of the intestinal tract, optionally in a delayed manner, examples of embedding compositions which can be used being polymeric substances and waxes.

The active compound or compounds, optionally together with one or more of the abovementioned excipients, can also be in a microencapsulated form.

Suppositories can contain, in addition to the active compound or compounds, the customary water-soluble or water-insoluble excipients, for example polyethylene glycols, fats, for example cacao fat, and higher esters (for example $C_{14}$-alcohol with $C_{16}$-fatty acid), or mixtures of these substances.

Ointments, pastes, creams and gels can contain, in addition to the active compound or compounds, the customary excipients, for example animal and vegetable fats, waxes, paraffins, starch, tragacanth, cellulose derivatives, polyethylene glycols, silicones, bentonites, silica, talc and zinc oxide, or mixtures of these substances.

Powders and sprays can contain, in addition to the active compound or compounds, the customary excipients, for example lactose, talc, silica, aluminum hydroxide, calcium silicate and polyamide powders, or mixtures of these substances, and sprays can additionally contain the customary propellants, for example chlorofluoro hydrocarbons.

Solutions and emulsions can contain, in addition to the active compound or compounds, the customary excipients, such as solvents, solution retarders and emulsifiers, for example water, ethyl alcohol, isopropyl alcohol, ethyl carbonate, ethyl acetate, benzyl alcohol, benzylbenzoate, propylene glycol, 1,3-butylene glycol, dimethylformamide, oils, in particular cottonseed oil, groundnut oil, maize germ oil, olive oil, castor oil and sesame oil, glycerol, glycerol formal, tetrahydrofuryl alcohol, polyethylene glycols and fatty acid esters of sorbitan, or mixtures of these substances.

For parenteral administration, the solutions and emulsions can also be in a sterile form which is isotonic with blood.

Suspensions can contain, in addition to the active compound or compounds, the customary excipients, such as liquid diluents, for example, water, ethyl alcohol and propyl alcohol, suspending agents, for example ethoxylated isostearyl alcohols, polyoxyethylene sorbitol esters and sorbitan esters, microcrystalline cellulose, aluminium metahydroxide, bentonite, agar-agar and tragacanth, or mixtures of these substances.

The formulation forms mentioned can also contain colorants, preservatives and additives which improve the odor and flavour, for example peppermint oil and eucalyptus oil, and sweeteners, for example saccharin.

The therapeutically active compounds should preferably be present in the abovementioned pharmaceutical formulations in a concentration of about 0.1 to 99.5, preferably 0.5 to 95% by weight of the total mixture.

The abovementioned pharmaceutical formulations can also contain other pharmaceutically active compounds, in addition to the active compounds according to the invention.

The abovementioned pharmaceutical formulations are prepared in the customary manner by known methods, for example by mixing the active compound or compounds with the excipient or excipients.

The present invention also includes the use of the active compounds according to the invention, and of pharmaceutical formulations which contain one or more active compounds according to the invention, in human and veterinary medicine for the prevention, alleviation and/or cure of the abovementioned diseases.

The active compounds or the pharmaceutical formulations can be administered locally, orally, parenterally, intraperitoneally and/or rectally, preferably parenterally and in particular intravenously.

In general, it has proved advantageous both in human medicine and in veterinary medicine to administer the active compound or compounds in total amounts of about 2.5 to about 200, preferably 5 to 150 mg/kg of body weight every 24 hours, optionally in the formof several individual doses, to achieve the desired results.

In the case of oral administration, the active compounds according to the invention are administered in total amounts of about 2.5 to about 200, preferably 5 to 150 mg/kg of body weight every 24 hours, and in the case of parenteral administration they are administered in total amounts of about 2.5 to about 50, preferably 1 to 25 mg/kg of body weight every 24 hours.

However, it may be necessary to deviate from the dosages mentioned, and in particular to do so as a function of the species and body weight of the subject to be treated, the nature and severity of the disease, the nature of the formulation and of the administration of the medicament, and the time or interval over which the administration takes place. Thus it can in some cases suffice to manage with less than the abovementioned amount of active compound, while in other cases the abovementioned amount of active compound must be exceeded. The particular optimum dosage required and the type of administration of the active compound can easily be determined by any one skilled in the art on the basis of his expert knowledge.

PREPARATION EXAMPLES

Example 1

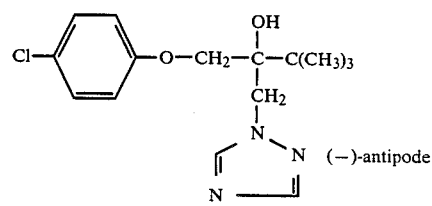

1st stage

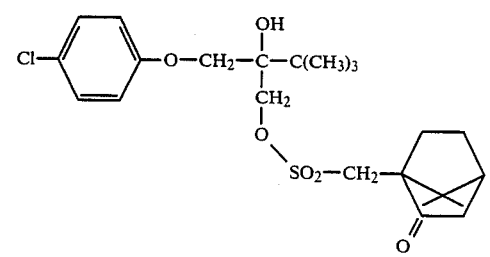

12.5 g (0.05 mole) of d(+)-camphor-10-sulphonic acid are added to 12 g (0.05 mole) of racemic 2-(4-chlorophenoxymethyl)-2-tert.-butyl-oxirane in 150 ml of acetonitrile at 20° C., with stirring. The mixture is left to stand overnight at room temperature, poured into water and extracted with methylene chloride. The organic phase is washed twice with water, dried over magnesium sulphate and concentrated in vacuo. 18 g of a diastereomer mixture of 2-(4-chlorophenoxymethyl)-3,3-dimethyl-2-hydroxy-1-butyl d(+)-camphor-10-sulphonate are obtained as a viscous oil, from which a pure diastereomer (melting point: 103° C.) partly crystallizes out.

The diastereomer mixture is separated by means of HPLC on silica gel in the system hexane/isopropyl ether. This gives
(a) 5.2 g of *fraction* 1 as a colourless oil with an optical rotation $[\alpha]_D^{20} = +21.6°$ (CHCl$_3$, C=0.67) and
(b) 5.0 g of *fraction* 2 of melting point 103° C. with an optical rotation of $[\alpha]_D^{20} = +32.8°$ (CHCl$_3$, C=1.02).

2nd stage

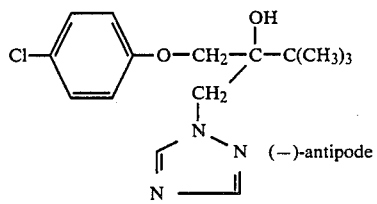

5.2 g (11 mmol) of 2-(4-chlorophenoxymethyl)-3,3-dimethyl-2-hydroxy-1-butyl d(+) camphor-10-sulphonate according to *fraction* 1 of the first stage are heated under reflux with 3 g (43 mmol) of 1,2,4-triazole and 3 g (21 mmol) of potassium carbonate in 60 ml of acetonitrile for 8 hours, with stirring. The reaction mixture is then poured onto water and extracted with methylene chloride and the organic phase is concentrated. The crude product is purified by means of column chromatography in the system chloroform/ethyl acetate (3:1). 2.2 g (68% of theory) of the (−)-antipode of 2-(4-chlorophenoxymethyl)-3,3-dimethyl-1-(1,2,4-triazol-1-yl)-2-butanol of melting point 57° C. and with an optical rotation of $[\alpha]_D^{20} = -111.4°$ (CHCl$_3$) are obtained.

Example 2

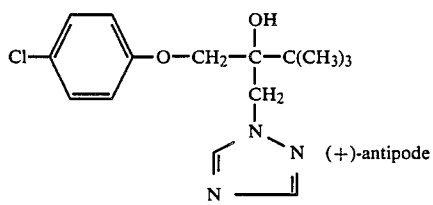

1st stage

In this context, compare Example 1, 1st stage, fraction 2.

2nd stage

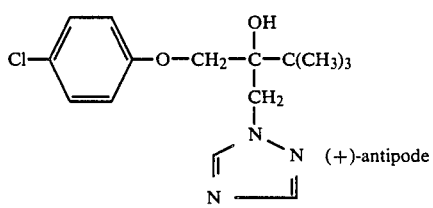

8.0 g (17 mmol) of 2-(4-chlorophenoxymethyl)-3,3-dimethyl-2-hydroxy-1-butyl d(+) camphor-10-sulphonate according to *fraction* 2 of the 1st stage of Example 1 are heated under reflux with 5 g (72 mmol) of 1,2,4-triazole and 5 g (35 mmol) of potassium carbonate in 80 ml of acetonitrile for 8 hours, with stirring. The reaction mixture is then poured onto water and extracted with methylene chloride and the organic phase is concentrated. The oily residue is dissolved in cyclohexane. The symmetric triazole derivative thereby crystallises out (1.2 g of melting point 220° C.), and is filtered off.

The filtrate is concentrated in vacuo and the oily residue is made to crystallise with petroleum ether. 3.2 g (57% of theory) of the (+) antipode of 2-(4-chlorophenoxymethyl)-3,3-dimethyl-1-(1,2,4-triazol-1-yl)-2-butanol of melting point 57° C. with an optical rotation of $[\alpha]_D^{20} = +113°$ C. (CHCl$_3$) are obtained.

USE EXAMPLES

Example A

Sterol synthesis inhibition by *Candida albicans*

Description of the experiment:

Culture of the microbes and incubation with the active compounds:

250 ml narrow-necked conical flasks were filled with 95 ml of Kimmig nutrient solution and closed with tightly fitting cottonwool plugs. Kimmig medium has the following composition:

| | |
|---|---|
| Nutrient broth (Difco 003) | 13 g |
| Glycerol, analytical grade | 5 g |
| Bacto-Peptone (Difco 0118) | 8.6 g |
| Glucose | 10 g |
| NaCl, analytical grade | 9 g |
| Demineralized water to | 1000 g |

After sterilization (15 minutes at 120° C.), the flasks were inoculated. Inoculation was carried out with: 48-hour cultures on Kimmig slant tubes. For flotation, sterile physiological NaCl solution was used, and the culture surfaces were scraped off with a glass spatula. The microbe suspensions were then filtered through sterile gauze filters. Microbe inocula of 5×10$^7$ microbes per 5 ml of Kimmig medium were prepared photometrically from the filtrates for each flask, and these were added to the flasks. The number of particles which are probably capable of germinating per ml of nutrient substrate in the flasks was thus about 5×10$^5$/ml.

After inoculation, the flasks were incubated in a shaking cabinet (clim-O-shake, A. Kuhner, Basle) at 28° C. with a shaking frequency of 95 rpm. The active compounds—in each case dissolved in 1 ml of absolute ethanol—are added immediately before the incubation. Only 1 ml of ethanol was added to the control flasks free from active compound.

The Candida cultures were incubated for 48 hours. After the incubation, the culture flasks containing growth were emptied into centrifuge glasses and these were centrifuged at 5000 rpm for 15 minutes. After the centrifugate had been washed with physiological NaCl solution and centrifuged again, the sedimented microbes were taken up in a mixture of chloroform and methanol (2:1) for further processing.

Extraction and isolation of the sterols was effected in accordance with Ann. Phytopathol. 10, 1980, 45.

Quantitative analysis was carried out by gas chromatography in accordance with *Phytochem.* 18, 1979, 445.

| Active compound | Concentration in ppm | Result Total amount of sterol | |
|---|---|---|---|
| | | in area units | in μ/20 ml of test batch |

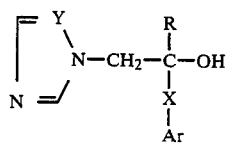

| | | | |
|---|---|---|---|
| | 1 | no growth visible | |
| (−)-antipode | 0.1 | 29.4 | 97.0 |
| (+)-antipode | 1 | 101.3 | 334.3 |
| (±)-racemate | 1 | 41.0 | 135.3 |
| Control | — | 164.4 | 542.5 |

These results show the unexpectedly better inhibition of sterol synthesis of the (−)-antipode according to the invention in comparison with the corresponding (+)-antipode and the racemate, which leads to better pharmacological properties of the (−)-antipode.

We claim:

1. Process for the preparation of an optically active azolylcarbinol derivative of the formula $$\begin{array}{c} Y \\ \diagdown \\ N-CH_2-\underset{\underset{Ar}{\overset{X}{|}}}{\overset{R}{\underset{|}{C}}}-OH \\ N = \diagup \end{array}$$

in which

Ar is phenyl optionally mono-, di- or tri-substituted, identically or differently by halogen, alkyl with 1 to 4 carbon atoms, alkoxy and alkylthio with in each case 1 or 2 carbon atoms, nitro, and halogenoalkyl, halogenalkoxy and halogenoalkylthio with in each case 1 or 2 carbon atoms and 1 to 3 identical or different halogen atoms, or phenyl, phenoxy, benzyl or benzyloxy, each of which is optionally substituted by halogen and/or alkyl with 1 or 2 carbon atoms, or the —CH=NOZ radical, wherein Z represents hydrogen, straight-chain or branched alkyl with 1 to 6 carbon atoms, alkenyl or alkynyl with in each case 2 to 6 carbon atoms, or benzyl which is optionally mono-, di- or tri-substituted by identical or different substituents from the group comprising halogen and alkyl with 1 or 2 carbon atoms;

R is

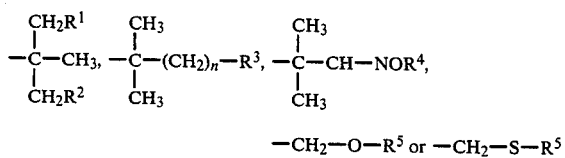

$$-CH_2-O-R^5 \text{ or } -CH_2-S-R^5$$

or is cycloalkyl which has 3 to 7 carbon atoms and is optionally substituted by alkyl with 1 or 2 carbon atoms, or is cyclopropyl which is substituted by triazolyl or imidazolyl, or is phenyl which is optionally substituted by substituents on the phenyl, these being the substituents on phenyl which have already been mentioned for Ar;

wherein $R^1$ is hydrogen, fluorine, chlorine or bromine;

$R^2$ is fluorine, chlorine or bromine;

$R^3$ is alkyl, alkoxy or alkylthio with in each case 1 to 4 carbon atoms, halogenoalkoxy or halogenoalkylthio with in each case 1 or 2 carbon atoms and 1 to 5 identical or different halogen atoms, alkenyl with 2 to 6 carbon atoms, alkoxycarbonyl with 1 to 6 carbon atoms in the alkyl part, or cyano, or is phenyl, phenoxy, phenylthio, benzyloxy or benzylthio, each of which is optionally substituted on the phenyl by halogen, alkyl with 1 to 4 carbon atoms, alkoxy and alkylthio with in each case 1 or 2 carbon atoms, halogenoalkyl, with in each case 1 or 2 carbon atoms and 1 to 5 identical or different halogen atoms, dialkylamino with 1 to 4 carbon atoms in each alkyl part, nitro, cyano, alkoxycarbonyl with 1 to 4 carbon atoms in the alkyl part, and phenyl which is optionally substituted by halogen;

n is 0, 1 or 2;

$R^4$ is alkyl with 1 to 6 carbon atoms or alkenyl or alkynyl with in each case 2 to 6 carbon atoms, or is phenylalkyl which has 1 or 2 carbon atoms in the alkyl part and is optionally substituted by substituents on the phenyl, these being the substituents on phenyl which have already been mentioned for Ar, $R^5$ is alkyl with 1 to 4 carbon atoms; and X is a group selected from —OCH$_2$—, —SCH$_2$—, —CH$_2$CH$_2$—, —CH=CH— and —C≡C— or a direct bond; and Y is a nitrogen atom or the —CH-group, characterized in that, in a first reaction step, an oxirane of the formula

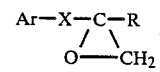

in which

Ar, R and X having the abovementioned meaning, are reacted with a strong optically active sulphonic acid, or with 1,1′-binaphthyl-2,2′-diylphosphate if appropriate in the presence of a solvent, the diasteriomeric ester mixture formed is separated into the diastereomerically pure components and these are reacted, in a second reaction step, with 1,2,4-triazole or imidazole in the presence of a base.

2. Process according to claim 1, wherein

Ar is phenyl which is optionally mono- or di-substituted by fluorine, chlorine, bromine, methyl, ethyl, isopropyl, tert.-butyl, methoxy, methylthio, trifluoromethyl, trifluoromethoxy, trifluoromethylthio, methoximinomethyl, butoximinomethyl and 1-methoxyiminoethyl, and phenyl, phenoxy, benzyl or benzyloxy, each of which is optionally substituted by fluorine, chlorine and/or methyl;

R is

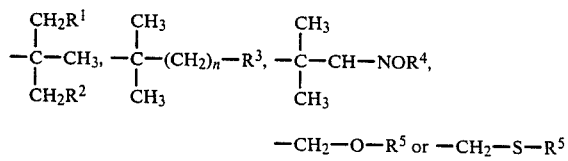

$$-CH_2-O-R^5 \text{ or } -CH_2-S-R^5$$

or is cyclopropyl, cyclopentyl or cyclohexyl, each of which is optionally substituted by methyl or ethyl, or is 1-(1,2,4-triazol-1-yl)- or (imidazol-1-yl)-1-cyclopropyl, or is phenyl which is optionally substituted by substituents from the group comprising fluorine, chlorine, methyl and trifluoromethyl, $R^1$ is hydrogen, fluorine or chlorine;

$R^2$ is fluorine or chlorine;

$R^3$ is methyl, ethyl, propyl, methoxy, ethoxy, methylthio, ethylthio, trifluoromethoxy, trifluoromethylthio, vinyl, methoxycarbonyl, ethoxycarbonyl or cyano, or is phenyl, phenoxy, phenylthio, phenoxymethoxy or phenylmethylthio, each of which is optionally mono- or di-substituted by substituents on the phenyl selected from fluorine, chlorine, methyl, ethyl, methoxy, methylthio, trifluoromethyl, trifluoromethoxy, trifluoromethylthio, dimethylamino, methoxycarbonyl or ethoxycarbonyl, n is 0, 1 or;

$R^4$ is methyl, ethyl, n-propyl, n-butyl, allyl or propargyl, or is benzyl which is optionally mono- or di-substituted by substituents from the group comprising fluorine, chlorine, methyl, trifluoromethyl and trifluoromethoxy;

$R^5$ is methyl, ethyl, isopropyl, n-propyl, n-butyl or isobutyl;

X is —OCH$_2$—, —SCH$_2$—, —CH$_2$CH$_2$—, —CH=CH— or —C≡C— or a direct bond.

3. Process according to claim 1, wherein

Ar is phenyl which is substituted by radicals from the group comprising fluorine, chlorine and phenyl and R is the radical

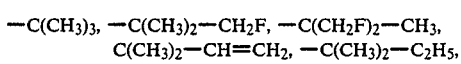

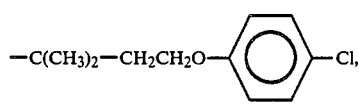

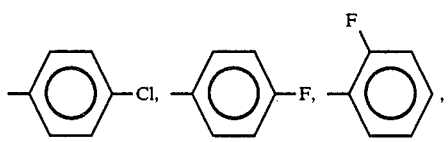

-continued

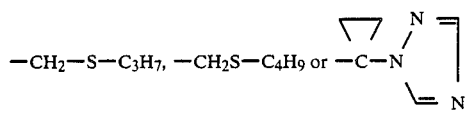

and

X is —OCH$_2$—, —SCH$_2$—, —CH$_2$CH$_2$—, —CH=CH— or —C≡C— or a direct bond.

4. Process for the preparation of the (—)-enantiomer of 2-(4-chlorophenoxymethyl)-3,3-dimethyl-1-(1,2,4-triazol-1-yl)-2-butanol of the formula

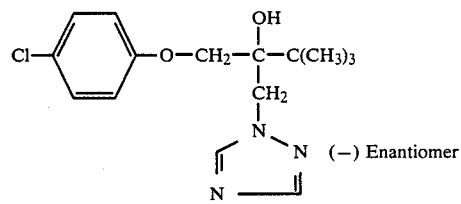

(—) Enantiomer and its physiologically acceptable acid addition products, characterized in that racemic 2-(4-chlorophenoxymethyl)-2-tert.-butyloxirane of the formula

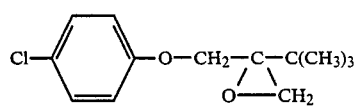

is first reacted with a strong optically active acid, if appropriate in the presence of a solvent, the corresponding diastereomeric ester mixture is separated into the diastereomerically pure components and reaction is then carried out with 1,2,4-triazole in the presence of a diluent, if appropriate in the presence of a base, and, if appropriate, the product is converted into its salts.

5. Process according to claim 1, wherein the strong optically active sulfonic acid is camphor-10-sulfonic acid, 3-bromo-10-camphorsulfonic acid, 3-bromo-8-camphorsulfonic acid.

6. Process according to claim 1, wherein the first reaction step is carried out in the temperature range from 0° to 100° C., and the second step is carried out in the temperature range from 0° to 150° C.

7. Process according to claim 1, wherein the first reaction step, equimolar amounts of the components are reacted, and in the second reaction step, 1 to 4 moles of triazole or imidazole and, if appropriate, 1 to 2 moles of base are reacted per mole of ester.

8. Process of claim 1, wherein said first reaction step is carried out, in the absence of a catalyst.

* * * * *

UNITED STATES PATENT AND TRADEMARK OFFICE
CERTIFICATE OF CORRECTION

PATENT NO. : 4,783,538

DATED : Nov. 8, 1988

INVENTOR(S) : Kraatz et al.

It is certified that error appears in the above-identified patent and that said Letters Patent is hereby corrected as shown below:

Col. 8, line 56  Correct number --P 34 40 118.0--

Col. 10, line 38  Delete "a" in third instance

Col. 14, line 11  Delete "formof" and substitute --form of --

Signed and Sealed this

Twenty-third Day of January, 1990

Attest:

JEFFREY M. SAMUELS

Attesting Officer  Acting Commissioner of Patents and Trademarks